(12) United States Patent
Kaneda et al.

(10) Patent No.: US 7,785,889 B2
(45) Date of Patent: Aug. 31, 2010

(54) FOOD ASTRINGENCY EVALUATING METHOD USING LIPID MEMBRANE SENSORS WITH IMMOBILIZED PEPTIDES

(75) Inventors: Hirotaka Kaneda, Yaizu (JP); Yoshio Okahata, Kawasaki (JP)

(73) Assignee: Sapporo Breweries Limited, Tokyo (JP)

( * ) Notice: Subject to any disclaimer, the term of this patent is extended or adjusted under 35 U.S.C. 154(b) by 542 days.

(21) Appl. No.: 10/105,392

(22) Filed: Mar. 26, 2002

(65) Prior Publication Data

US 2004/0086607 A1    May 6, 2004

(30) Foreign Application Priority Data

Mar. 27, 2001   (JP)   ............... 2001-090878

(51) Int. Cl.
*G01N 33/14*   (2006.01)
(52) U.S. Cl. .............. 436/24; 436/20; 436/71; 436/86; 436/151
(58) Field of Classification Search ............ 436/20, 436/24, 86, 87, 127, 128, 131, 88
See application file for complete search history.

(56) References Cited

U.S. PATENT DOCUMENTS

| | | | | |
|---|---|---|---|---|
| 5,482,855 | A | * | 1/1996 | Yamafuji et al. ........ 204/403.06 |
| 5,785,984 | A | * | 7/1998 | Kurihara et al. ............. 424/439 |
| 5,789,250 | A | * | 8/1998 | Ikezaki ........................ 436/20 |
| 6,057,160 | A | | 5/2000 | Silber et al. |

FOREIGN PATENT DOCUMENTS

EP   0 410 356   1/1991

OTHER PUBLICATIONS

Journal of Agricultural Food Chemistry. "Polyphenol/Peptide Binding and Precipitation". Charlton et al. Feb. 2002.*
Journal of Food Science. "Adsorption of Tannins on Lipid Membrane in the Presence of Peptides as Related to Astringency". Kaneda et al. Nov. 2002.*
Journal of Agricultural Food Chemistry. "New Method for Evaluating Astringency in Red Wine". Jan. 2004.*
Biochemistry. "Multiple Interactions between Polyphenols and a Salivary Proline-Rich Protein Repeat Result in Complexation and Precipitation". Baxter et al. 1997.*
Biochemistry. "Three Dimensional Structure and Dynamics of Wine Tannin-Saliva Protein Complexes. A Multitechnique Approach". Simon et al. Aug. 2003.*
Iiyama et al. "Response of lipid membranes of taste sensor to astringent and pungent substances", Chem. Senses., 1994, v. 19, No. 1, pp. 87-96, Abstract.*
Takagi et al. "Detection of suppression of bitterness by sweet substance using a multichannel taste sensor", J. Pharm. Sci., 1998, v. 87, No. 5, pp. 552-555.*

(Continued)

*Primary Examiner*—Yelena G Gakh
(74) *Attorney, Agent, or Firm*—Oblon, Spivak, McClelland, Maier & Neustadt, L.L.P.

(57) ABSTRACT

The food astringency evaluating method of the invention comprises a step in which an astringent component of a food is reacted with a peptide to form a complex, a step in which a prescribed measured value is obtained corresponding to the amount of formation of the complex, and a step in which the strength of astringency is determined from the obtained measured value based on a previously obtained correlation between strength of astringency and the prescribed measured value.

22 Claims, 12 Drawing Sheets

OTHER PUBLICATIONS

Toko, "Biomimetic Sensor Technology", Cambridge University Press 2000, Contents and Preface.*

Murray et al. "Study of the interaction between salivary proline-rich proteins and a polyphenol by 1H-NMR spectroscopy", Eur. J. Biochem., 1994, v. 219, pp. 923-935.*

Baxter et al. "Multiple interactions between polyphenols and a salivary proline-rich proteins repeat result in complexation and precipitation", Biochemistry, 1997, v. 36, pp. 5566-5577.*

Naishi et al. "Effect of gelatin (a model for salivary PRP) on the sensory astringency of 5-O-caffeoylquinc acid and tannic acid", Annals NY Acad. Sci., 1998, v. 855, pp. 823-827.*

Bacon et al. "Binding affinity of hydrolyzable tannins to parotid saliva and to proline-rich proteins derived from it", J. Agric. Food Chem., 2000, v. 48, pp. 838-843.*

Clement et al. "Novel Multigene Families Encoding Highly Repetitive Peptide Sequences", J. Biol. Chem., 1985, vol. 260, No. 25, pp. 13471-13477.*

Barry G. Green. et al., "Derivation and Evaluation of a Semantic Scale of Oral Sensation Magnitude with Apparent Ratio Properties", Oxford University Press, 1993, pp. 683-702.

Hirotaka Kaneda, et al., "Adsorption to or Desorption of Beer Components from a Lipid Membrane Related to Sensory Evaluation", Journal of Bioscience and Bioengineering, vol. 92, No. 3, XP-002286940, 2001, pp. 221-226.

Peter Hauptmann, et al., "Artificial Electronic Tongue in Comparison to the Electronic Nose-State of the Art and Trends", 2000 IEEE/EIA International Frequency Control Symposium and Exhibition, XP-010525518, 2000, pp. 22-29.

Douglas O. Adams, et al., "Use of Alkaline Phosphatase for the Analysis of Tannins in Grapes and Red Wines", American Journal of Enology and Viticulture, vol. 50, No. 3, XP-009033171, 1999, pp. 247-252.

Derwent Publications, AN 2000-385305, XP-002286942, RU 2 127 878, Mar. 20. 1999.

* cited by examiner

FOOD ASTRINGENCY EVALUATING METHOD USING LIPID MEMBRANE SENSORS WITH IMMOBILIZED PEPTIDES

BACKGROUND OF THE INVENTION

1. Field of the Invention

The present invention relates to a food astringency evaluating method and astringency evaluating apparatus, and more specifically it relates to a method and apparatus which are useful for quantitative evaluation of the astringency of foods such as beer, wine, green tea and the like.

2. Related Background Art

Food flavor is judged based on human gustation, and traditional evaluation of food flavor has generally been carried out by organoleptic evaluation tests. An organoleptic evaluation test is an evaluation conducted with prescribed evaluation parameters using a sensory scale known in the field of psychology (psychophysics), such as a category scale, magnitude scale, labeled magnitude scale, etc. (Green, B. et al., Chemical Senses, 18, 683(1993)). In the case of beer, for example, several types of beer samples are prepared and taste-tested by subjects, and the taste is evaluated with respect to the parameters of "bitterness strength or residue", "astringency strength or residue", "richness", "smoothness", etc., based on the gustation of the subjects.

Of these gustation parameters, "astringency" is an extremely important factor in evaluating excellent flavor for beer, wine, green tea and the like, and a quantitative evaluation of astringency is preferred for the development of such foods that are recently being subjected to an ever widening diversity of personal tastes.

SUMMARY OF THE INVENTION

However, astringency is evaluated in organoleptic evaluation tests according to the gustation of the subjects, and the term "astringency" is interpreted in different ways by different people. Hence, quantitative evaluation of food astringency has necessitated much time and effort for increasing the number of subjects and increasing the number of tests conducted for each subject.

It is an object of the present invention, which has been accomplished in light of these problems of the prior art, to provide a method and apparatus which allow adequately precise and simple quantitative evaluation of astringency when the astringency of foods such as beer, wine, green tea and the like are evaluated.

As a result of much diligent research directed toward achieving this object, the present inventors have completed the present invention upon finding that it is possible to achieve adequately precise and simple quantitative evaluation of astringency by reacting the astringent component of a food with a peptide to form a complex, obtaining a given measurement corresponding to the amount of formation of the complex or the amount of adsorption of the complex onto a lipid membrane, and then determining the strength of astringency from the obtained measurement based on a previously obtained correlation between strength of astringency and the given measurement corresponding to amount of formation or adsorption.

In other words, the first method of the invention is a food astringency evaluating method, which comprises:

a complex formation step in which an astringent component of a food is reacted with a peptide to form a complex, a complex formation measuring step in which a prescribed measured value is obtained corresponding to the amount of formation of the complex, and an astringency evaluation step in which the strength of astringency is determined from the measured value obtained in the complex formation measuring step based on a previously obtained correlation between strength of astringency and the prescribed measured value.

The second method of the invention is a food astringency evaluating method, which comprises:

a complex formation step in which an astringent component of a food is reacted with a peptide to form a complex, a complex adsorption measuring step in which a prescribed measured value is obtained corresponding to the amount of adsorption of the complex onto a lipid membrane using a lipid membrane sensor, and an astringency evaluation step in which the strength of astringency is determined from the measured value obtained in the complex adsorption measuring step based on a previously obtained correlation between strength of astringency and the prescribed measured value.

Moreover, the first apparatus of the invention is a food astringency evaluating apparatus, which comprises:

a sensor for measuring the amount of formation of a complex obtained by reaction of an astringent component of a food with a peptide, and data processing means for determining the strength of astringency from the measured value obtained by the sensor based on a previously obtained correlation between strength of astringency and the amount of formation of the complex, which is in electrical connection with the sensor.

The second apparatus of the invention is a food astringency evaluating apparatus, which comprises:

a lipid membrane sensor for obtaining a prescribed measured value corresponding to the amount of adsorption onto a lipid membrane by a complex obtained by reaction of an astringent component of a food with a peptide, and data processing means for determining the strength of astringency from the measured value obtained by the lipid membrane sensor based on a previously obtained correlation between strength of astringency and the prescribed measured value, which is in electrical connection with the lipid membrane sensor.

According to the invention, the prescribed measured value corresponding to the amount of formation of the complex formed upon reaction of the astringent component of the food with the peptide, or to the amount of adsorption of the complex onto the lipid membrane, is obtained in a simple and easy manner and with a high degree of reproducibility. In addition, with the data processing means it is possible to make an online determination of the strength of astringency from the obtained measured value based on a previously obtained correlation between strength of astringency and the prescribed measured value corresponding to the amount of formation or amount of adsorption of the complex. It is thereby possible to accomplish adequately precise and simple quantitative evaluation of astringency with the food astringency evaluating method and astringency evaluating apparatus of the invention.

The present invention thus employs a prescribed measured value corresponding to the amount of formation of a complex between the astringent component of a food and a peptide, or the amount of adsorption of the complex onto a lipid membrane, and the present inventors surmise the following to be the reason why adequately precise quantitative evaluation of astringency of foods is possible based on these measured values.

Specifically, the astringency of a food is perceived by contact stimulus when the astringent components react with peptides inside the mouth to form a complex and the complex is adsorbed onto the lipid membrane of the tongue, and it is thought that the sweetness, bitterness, etc. perceived by this flavor stimulus is based on differences in this perception mechanism. The present inventors surmise that, since according to the invention it is possible to obtain the amount of complex formation or a given measurement with adequate precision correlating with the contact stimulus for this astringency perception mechanism, it is thereby possible to achieve an adequately precise quantitative evaluation of food astringency.

According to the invention, the food is preferably at least one type selected from the group consisting of beer, wine and green tea.

Moreover, according to the invention the astringent component is preferably at least one type selected from the group consisting of tannic acid, catechin, epicatechin, epigallocatechin gallate, quercetin, anthocyanidin and polyphenone 100.

Also, according to the invention the peptide is preferably at least one type selected from the group consisting of mouse proline-rich peptides, polyproline, gelatin and albumin.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
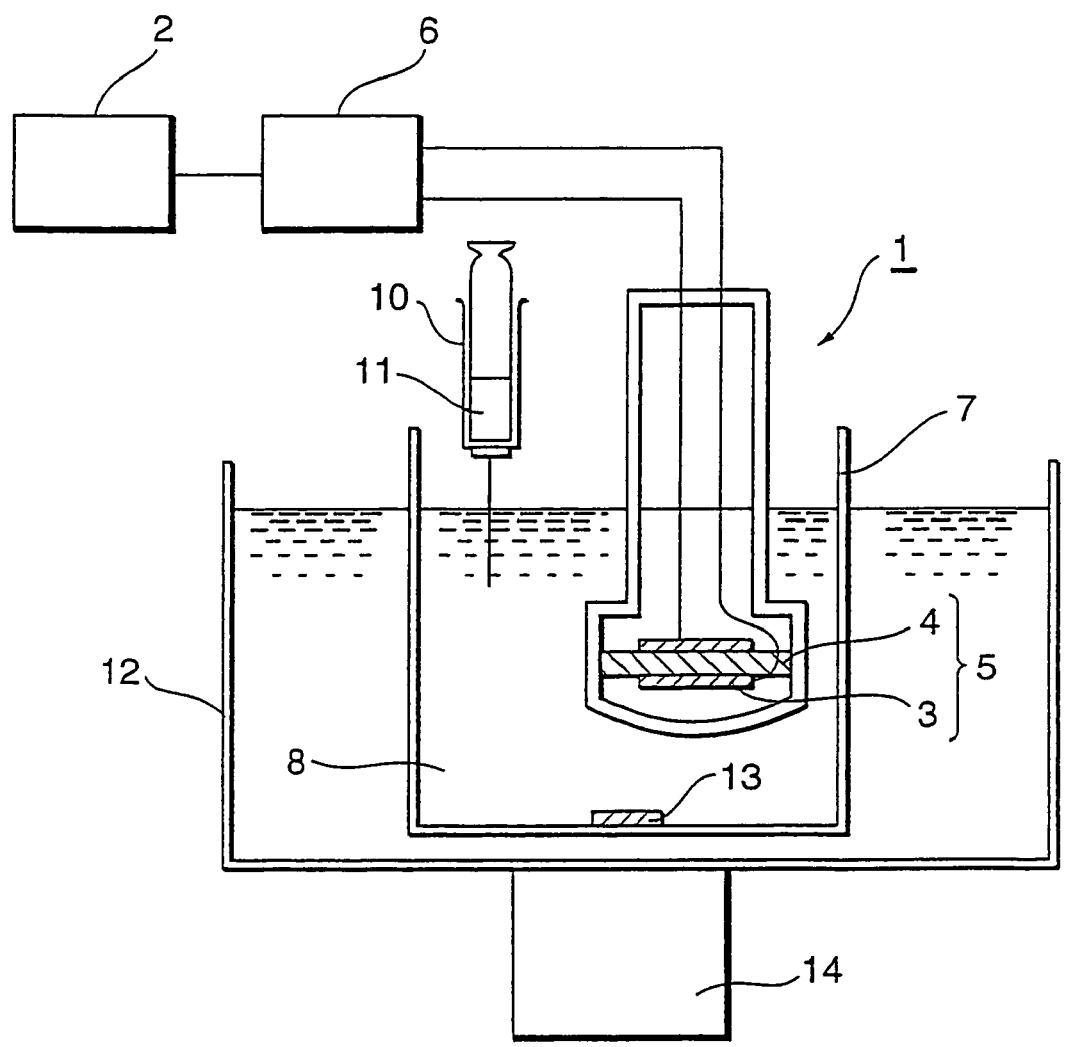
FIG. 1 is an abbreviated schematic diagram showing a preferred embodiment of the first apparatus of the invention.

A preferred embodiment of the invention will now be explained in detail with reference to the attached drawings.

The first method of the invention will be explained first.

The complex formation step of the first method of the invention forms a complex by reaction between an astringent component of a food and a peptide.

The food to be used for the invention is not particularly restricted, but the astringency evaluating method of the invention is highly useful for evaluation of the astringency of foods such as beer, wine and green tea for which astringency is an important factor in evaluating excellent taste.

As the astringent components of these foods there may be mentioned tannic astringent components, for example. As specific tannic astringent components there may be mentioned organic acids such as tannic acid, citric acid and malic acid, and polyphenols such as catechin, epicatechin, epigallocatechin gallate, quercetin, anthocyanidin and polyphenone 100.

The peptide according to the invention is not particularly restricted so long as it can form a complex with the aforementioned astringent component, and using a proline-containing peptide such as the peptide with the sequence listed as SEQ. ID. No. 1 of the attached Sequence Listing (hereunder referred to as "proline-rich peptide"), gelatin, poly-L-proline or bovine serum albumin is preferred because this will tend to give a higher level of precision for the prescribed measured value corresponding to the amount of adsorption of the complex onto the lipid membrane in the complex formation measuring step described hereunder. There are no particular restrictions on the molecular weight of the peptide used for the invention, but a range of a few thousand to a few tens of thousands is preferred for the weight-average molecular weight of the peptide.

For the complex formation step, the amounts of the food astringent component and peptide used for their reaction are not particularly restricted, but the amount of peptide used is preferably 100-15,000 parts by weight with respect to 100 parts by weight of the food astringent component. The reaction conditions may be appropriately set according to the types and amounts of astringent component and peptide used, but the reaction temperature is preferably 20-25° C. and the reaction time is preferably 0.5-10 minutes.

In the complex formation measuring step, the amount of complex formed in the complex formation step is measured using a sensor.

The sensor used for the complex formation measuring step is not particularly restricted so long as it can yield a prescribed measured value corresponding to the amount of formation of the complex, and for example, a sensor having the peptide immobilized on the electrode of a quartz oscillator may be used. When using such a sensor, it is possible to achieve adequately precise measurement of the oscillation frequency change corresponding to the amount of complex formation occurring upon formation of the complex by reaction between the peptide immobilized on the electrode and the food astringent component.

When a sensor having the peptide immobilized on an electrode is used for the complex formation measuring step, the sensor may be immersed into the food for measurement, or a solution containing the food astringent component may be prepared in advance and the sensor immersed in the solution for measurement. When using a sensor not having the peptide immobilized on an electrode, the peptide may be added to the food and the sensor immersed in the mixture for measurement, or else a solution containing the food astringent component and the peptide may be prepared in advance and the sensor immersed in the solution for measurement. The solvent used for preparation of such a solution may be, specifically, water, a buffer solution or the like, and water or a buffer solution is preferred. Using water or a buffer solution as the solvent will tend to result in a longer life for the lipid membrane sensor. Also, using such a solvent and adjusting the pH of the solution to within a prescribed range will tend to give higher precision for the prescribed measured value corresponding to the amount of formation of the complex or the amount of adsorption of the complex onto the lipid membrane.

There are no particular restrictions on the measuring conditions for the complex formation measuring step, but the measurement is preferably carried out under consistent temperature conditions in order to eliminate the temperature-dependent effects of adsorption of the astringent component and peptide complex onto the lipid membrane. As one method for maintaining consistent temperature conditions there may be mentioned, for example, a method in which a solution containing the food astringent component and the peptide is housed in a vessel and the sensor is immersed in the solution for measurement while the vessel is held in a water bath kept at a constant temperature.

For the astringency evaluation step, the strength of astringency of the food is determined from the measured value obtained in the aforementioned complex formation measuring step based on a previously obtained correlation between strength of astringency and the prescribed measured value.

Here, the correlation between the strength of astringency and the prescribed measured value is preferably established by conducting an organoleptic evaluation test of food astringency using a sensory scale widely employed in the field of psychology (psychophysics), such as a category scale, magnitude estimation, labeled magnitude scale, etc. The organoleptic evaluation test is preferably conducted using a magnitude estimation as the sensory scale, because this will tend to allow a more statistical treatment of the results directly in terms of strength.

Figure 2:
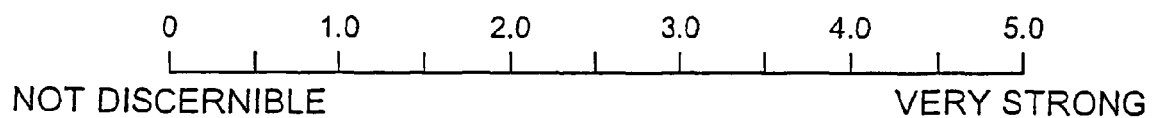
FIG. 2 is scale showing an example of a magnitude estimation used for organoleptic evaluation according to the invention.

An example of a magnitude estimation for organoleptic evaluation is shown in FIG. 2. For the magnitude estimation shown in FIG. 2, the maximum strength of "very strong" is assigned a value of 5.0, and the minimum strength of "not discernible" is assigned a value of 0, with a distance of 0.5 between each strength level. By using this sensory scale and assigning a score between 0 and 5.0 based on gustation of the subjects for food having known prescribed measured values corresponding to the formation of the complex, it is possible to obtain a correlation between the astringency of the food and the prescribed measured value.

The first method of the invention having the construction described above is preferably carried out using the first apparatus of the invention, described below.

FIG. 1 is an abbreviated schematic diagram showing a preferred embodiment of the first apparatus of the invention. The apparatus shown in FIG. 1 is provided with a sensor 1 and data processing means 2. The sensor 1 is provided with a quartz oscillator 5 constructed from an electrode 3 having a peptide immobilized on its surface and a quartz plate 4, and frequency measuring means 6 which is in electrical connection with the quartz oscillator 5, and it is positioned so that the quartz oscillator 5 is immersed in the solution 8 housed in the vessel 7. When an astringent component-containing solution 11 housed in a cylinder 10 is added to the solution 8, a control signal is sent from the frequency measuring means 6 to the quartz oscillator 5 while a data signal for the change in frequency is sent from the quartz oscillator 5 to the frequency measuring means 6, thus allowing measurement of the change in frequency which corresponds to the amount of formation of complex by reaction between the astringent component of the food and the peptide immobilized on the electrode 3. The data processing means 2 is electrically connected to the frequency measuring means 6, and a data signal for the change in frequency is sent from the frequency measuring means 6 to the data processing means 2. In the data processing means 2 there is stored a previously obtained correlation between astringency strength and change in frequency, and based on this correlation, the strength of astringency can be determined from the measurement obtained by the sensor 1.

This step may be carried out under any desired temperature condition by setting the vessel 7 in a thermostatic bath 12, as shown in FIG. 1. A stirrer 13 is also placed in the vessel 7 and the stirrer is rotated by stirring means 14 when the astringent component-containing solution 11 is added to the solution 8, to allow sufficiently uniform mixture of the solution 8 and solution 11.

The sensor used in the first apparatus of the invention is not particularly restricted so long as it can yield a prescribed measured value corresponding to the amount of formation of complex between the food astringent component and the peptide, but a sensor provided with a frequency oscillator (or more specifically, a quartz oscillator) with the peptide immobilized on its electrode, such as the sensor shown in FIG. 1, is preferred because its use will tend to give more precise measurement of the change in frequency corresponding to the complex formation.

Figure 3:
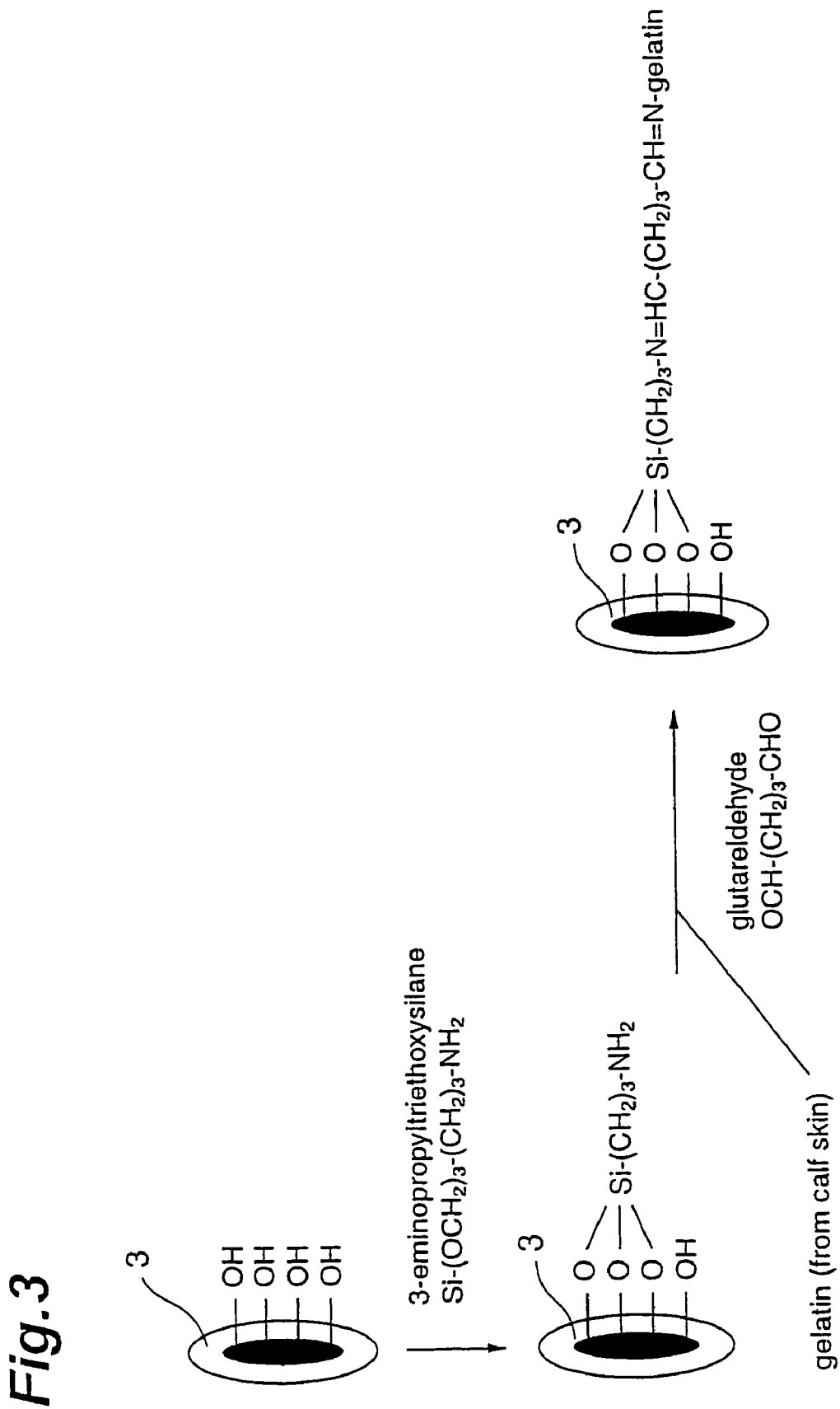
FIG. 3 is an illustration of an example of a method of immobilizing a peptide on the electrode surface of a sensor.

FIG. 3 is an illustration of an example of a method of immobilizing the peptide on the quartz oscillator electrode of the sensor. In FIG. 3, first hydrochloric acid or the like is used to activate the surface of the electrode 3 with hydroxyl groups oriented on the surface of the electrode 3, and then the hydroxyl groups on the surface of the electrode 3 are reacted with 3-aminopropyltrimethoxysilane to introduce amino groups onto the surface of the electrode 3. On the surface of the electrode 3 having amino groups introduced in this manner there is placed a glutaraldehyde-containing phosphate buffer solution (preferably pH 6.5-7.5 and more preferably pH 7.0), and gelatin heated to dissolution is further added to the phosphate buffer solution. The electrode may then be covered and sealed with Parafilm or the like and allowed to stand for a prescribed time to immobilize the gelatin on the electrode. The electrode obtained in this manner may be mounted on the sensor, to obtain a sensor having gelatin immobilized on the electrode (hereunder referred to as "gelatin sensor"). By using L-polyproline instead of the gelatin in FIG. 3, it is possible to obtain a sensor having L-polyproline immobilized on the electrode (hereunder referred to as "polyproline sensor").

The first method and first apparatus according to the invention having the construction described above can yield an adequately precise given measurement corresponding to the amount of formation of complex between a food astringent component and a peptide. In addition, by using data processing means for online determination of the astringency strength of food from the obtained measurement based on an already obtained correlation between the food astringency strength and the prescribed measured value, it is possible to measure the food astringency strength in a rapid and simple manner with a high level of reproducibility.

The second method of the invention will now be explained.

The complex formation step for the second method of the invention, like the first method described above, forms a complex by reaction between the astringent component of a food and a peptide. The foods, their astringent components and the peptides for the second method of the invention may be the same foods, astringent components and peptides mentioned for illustration in explaining the first method.

In the complex adsorption measuring step, a lipid membrane sensor is used to obtain a prescribed measured value corresponding to the amount of adsorption on to the lipid membrane by the complex formed in the aforementioned complex formation step.

The lipid membrane sensor used for the complex adsorption measuring step is not particularly restricted so long as it can yield a prescribed measured value corresponding to the amount of adsorption of the complex on to the lipid membrane, and there may be used a sensor provided with a frequency oscillator such as a quartz oscillator covered with a lipid membrane. A lipid membrane sensor provided with a frequency oscillator (especially a quartz oscillator) covered with a lipid membrane is preferred for use since this allows measurement of the change in frequency occurring upon adsorption or separation of the complex on to or from the lipid membrane, and this will tend to yield a given measurement corresponding to the amount of adsorption of the complex on to the lipid membrane with a higher degree of precision, without being affected by substances such as hydrogen ions and hydroxy ions that do not adsorb on to the lipid membrane.

There are no particular restrictions on the type of lipid membrane to be used for the lipid membrane sensor, and specifically there may be mentioned fatty acids and phospholipids; however, lipid membranes composed of dioctadecyldimethylammonium polystyrenesulfonic acid or dipalmitoyl phosphatidylethanolamine are preferred for use because they will tend to give higher precision for the prescribed measured value corresponding to the amount of adsorption of the complex on to the lipid membrane, and thus allow quantitative evaluation of food astringency with a high level of reproducibility.

In the complex adsorption measuring step, the lipid membrane sensor may be immersed in a solution containing the complex, and a prescribed measured value obtained corresponding to the amount of adsorption of the complex on to the lipid membrane. Here, the solvent for the food-containing solution may be water or a buffer solution, and water or a buffer solution is preferred. The pH of the complex-containing solution is preferably in the range of 3.5-5.0 since this will allow close simulation of the pH condition of actual food, and thus tend to yield the prescribed measured value at a higher precision.

When a solvent is used for the second method of the invention, the combination of the peptide and solvent is preferably selected as appropriate depending on the food or the astringent component in the food. For example, when the food is beer, a combination of gelatin and acetate buffer solution or a combination of gelatin and water is preferred, when the food is wine, a combination of albumin and acetate buffer solution is preferred, and when the food is green tea, a combination of albumin with water or acetate buffer solution is preferred. Using the aforementioned combinations of peptides and solvents will tend to give higher precision for the food astringency strength.

The measuring conditions for the complex adsorption measuring step are not particularly restricted, but measurement under consistent temperature conditions is preferred in order to eliminate the temperature-dependent effects of adsorption of the astringent component and peptide complex on to the lipid membrane. As one method for maintaining consistent temperature conditions there may be mentioned, for example, a method in which a solution containing the food astringent component and the peptide is housed in a vessel and the lipid membrane sensor is immersed in the solution for measurement while the vessel is held in a water bath kept at a constant temperature.

For the astringency evaluation step, the strength of astringency of the food is determined from the prescribed measured value obtained in the aforementioned complex adsorption measuring step based on a previously obtained correlation between strength of astringency and the prescribed measured value.

Here, the correlation between the strength of astringency and the prescribed measured value is preferably established by conducting an organoleptic evaluation test of food astringency using a sensory scale such as a category scale, magnitude estimation, labeled magnitude scale, etc., similar to the first method of the invention. The organoleptic evaluation test is preferably conducted using a magnitude estimation as the sensory scale, because this will tend to allow a more statistical treatment of the results directly in terms of strength.

The second method of the invention having the construction described above is preferably carried out using the second apparatus of the invention, described below.

Figure 4:
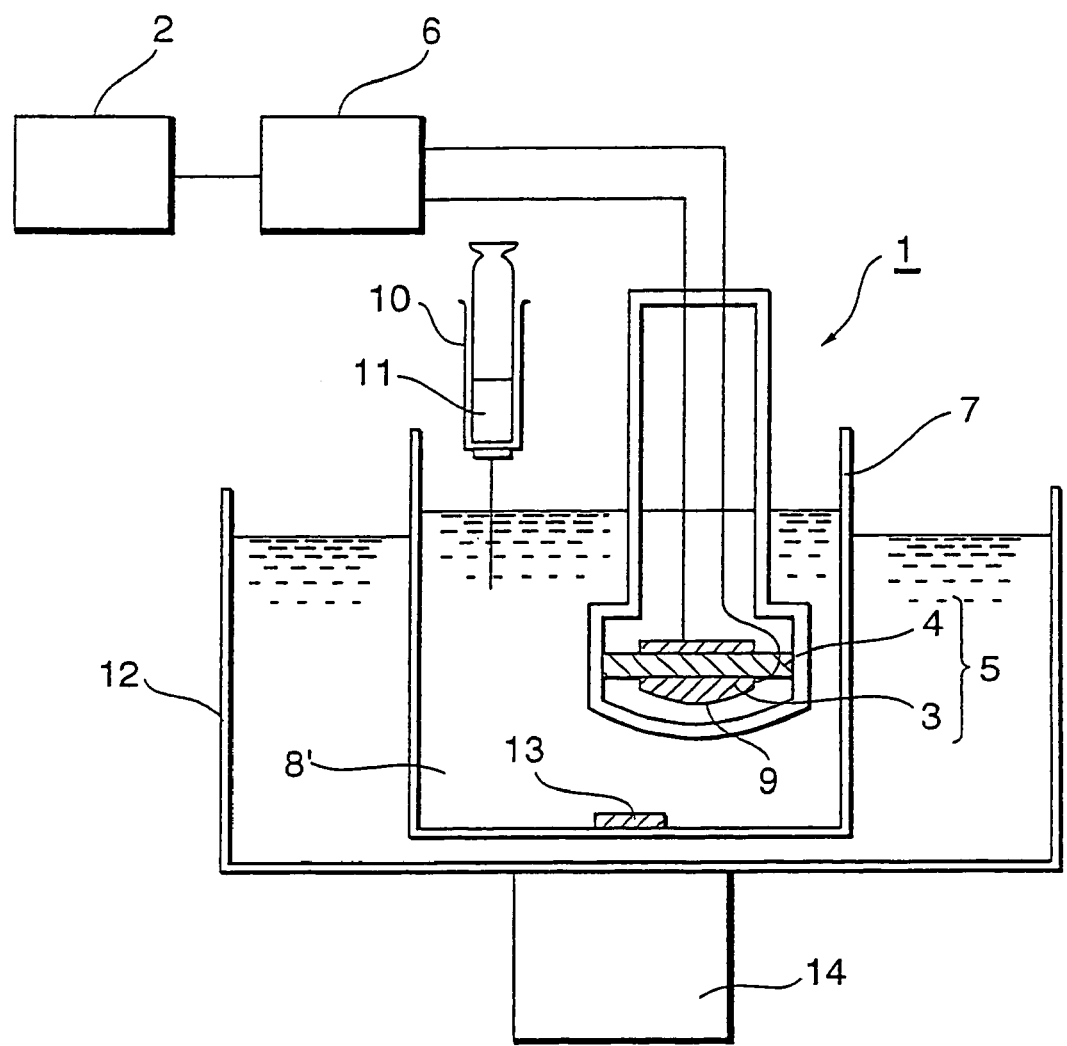
FIG. 4 is an abbreviated schematic diagram showing a preferred embodiment of the second apparatus of the invention.

FIG. 4 is an abbreviated schematic diagram showing a preferred embodiment of the second apparatus of the invention. The apparatus shown in FIG. 4 differs from the apparatus of FIG. 1 in that the electrode 3 of the quartz oscillator 5 of the sensor 1 is covered with a lipid membrane 9. Also, the sensor 1 is positioned so that the quartz oscillator 5 is immersed in the solution 8' containing the food astringency component and peptide which is housed in the vessel 7, and a control signal is sent from the frequency measuring means 6 to the quartz oscillator 5 while a data signal for the change in frequency is sent from the quartz oscillator 5 to the frequency measuring means 6, thus allowing measurement of the change in frequency which corresponds to the amount of adsorption of the food astringent component and peptide complex on to the lipid membrane 9. The data processing means 2 is electrically connected to the frequency measuring means 6, and a data signal for the change in frequency is sent from the frequency measuring means 6 to the data processing means 2. In the data processing means 2 there is stored a previously obtained correlation between astringency strength and change in frequency, and based on this correlation, the strength of astringency can be determined from the measured value obtained by the sensor 1.

The second method and second apparatus according to the invention having the construction described above can yield an adequately precise prescribed measured value corresponding to the amount of adsorption on to a lipid membrane by a complex between a food astringent component and a peptide. In addition, by using data processing means for online determination of the astringency strength of food from the obtained measured value based on an already obtained correlation between the food astringency strength and the prescribed measured value, it is possible to measure the food astringency strength in a rapid and simple manner with a high level of reproducibility.

EXAMPLES

The present invention will now be explained in greater detail by way of examples and comparative examples, with the understanding that the invention is in no way limited by these examples.

Example 1

Fabrication of Astringency Evaluating Apparatus with Gelatin Sensor

First, the gold electrode (diameter: 5 mm) of a sensor equipped with a quartz oscillator (Fragrance Sensor SF-105, product of Sogo Pharmaceutical Co., Ltd.) was immersed in 20 ml of a 1.2 N sodium hydroxide solution for 20 minutes, after which the electrode surface was washed with 500 ml of distilled water and immersed in 1.2 N dilute hydrochloric acid for 2 minutes. The electrode surface was then washed with distilled water and immersed in 12 N concentrated hydrochloric acid for 5 minutes, and the electrode was subsequently washed thoroughly with distilled water and dried at 100° C. for 20 minutes to obtain a quartz oscillator having hydroxyl groups arranged on the electrode surface.

After air-cooling the quartz oscillator, it was immersed in 0.3 ml of a 2% 3-aminopropyltriethoxysilane/acetone solution and allowed to stand at room temperature for 20 hours to introduce amino groups on to the electrode surface. The quartz oscillator was then subjected to ultrasonic washing treatment in 20 ml of acetone and dried at 70° C. for 90 minutes.

Next, 30 µl of 2.5% glutaraldehyde/20 mM phosphate buffer solution (pH 7.0) was placed on the amino group-introduced electrode surface, and the electrode was allowed to stand at room temperature for 2 hours. After then washing the electrode surface in 20 ml of 20 mM phosphate buffer solution and 20 ml of distilled water, it was mounted on an aqueous phase measuring sensor.

Next, 50 µl of a solution (0.5 mg/ml concentration) containing heat-dissolved gelatin (by Aldrich Chemical Company, Inc.) was placed on the electrode surface, the sensor element measuring section was covered and sealed with Parafilm and reaction was carried out overnight at room temperature, after which the electrode surface was washed with distilled water to obtain a gelatin sensor having 2 µg of gelatin immobilized on the electrode.

The gelatin sensor obtained in this manner was used to fabricate an astringency evaluating apparatus having the construction shown in FIG. 1.

(Correlation Between Amount of Complex Formation and Change in Frequency)

The obtained astringency evaluating apparatus was used for measurement of the change in frequency corresponding to formation of complex between catechin and gelatin according to the following procedure.

Figure 5:
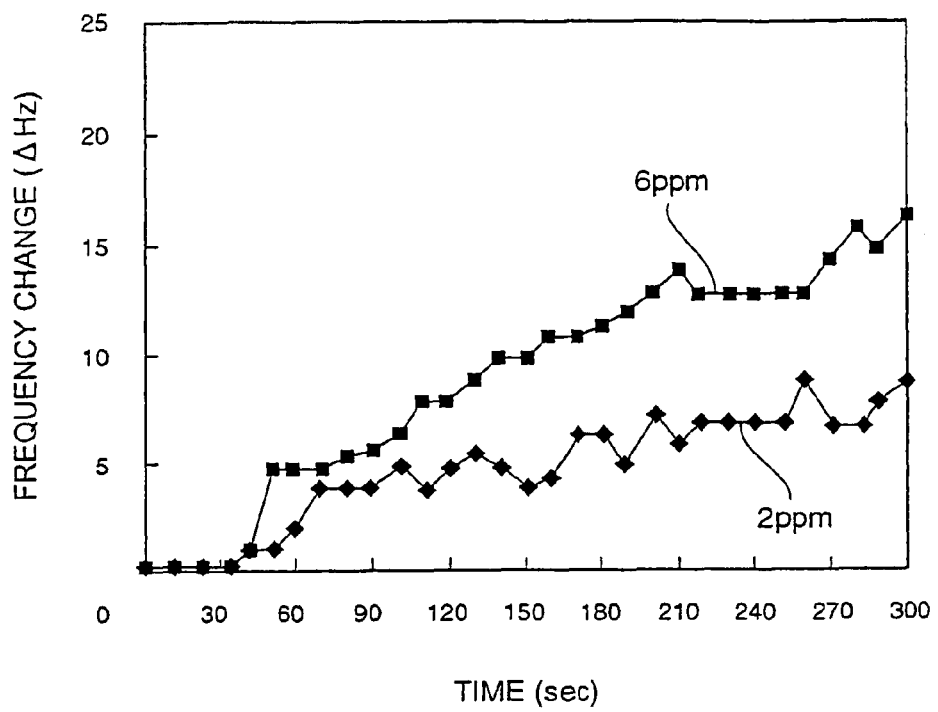
FIG. 5 is a graph showing the correlation between time and frequency change after addition of a catechin/ethanol solution, as obtained in Example 1.

First, the sensor element measuring section of the gelatin sensor was immersed for 30 seconds in 100 ml of distilled water, and stabilization of frequency was confirmed. Next, 0.1 ml of a catechin/ethanol solution was added to the distilled water, and the change in frequency was measured up to 4 minutes after addition. The above measurement was conducted using 2 different catechin/ethanol solutions with different catechin concentrations, for catechin concentrations of 2 ppm and 6 ppm immediately after addition to the distilled water. FIG. 5 shows the correlation between the time after addition of the catechin/ethanol solution and the change in frequency, as obtained by the measurement.

Figure 6:
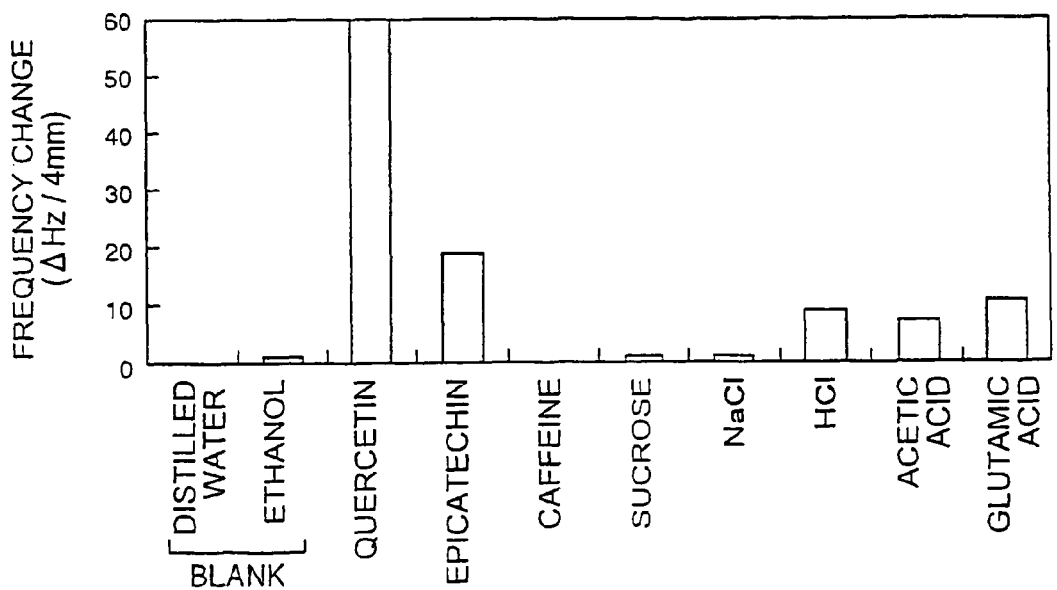
FIG. 6 is a graph showing the change in frequency with addition of each gustation component, as obtained in Example 1.

The change in frequency was also measured in the same manner as above except that quercetin/ethanol solutions and epicatechin/ethanol solutions were used instead of the catechin/ethanol solutions, and the astringency component concentration after addition to the distilled water was adjusted to 20 µM. As comparative tests, the same test was conducted using distilled water, ethanol, caffeine (bitter component)/ethanol solution, sucrose (sweet component) aqueous solution, NaCl (salty component) aqueous solution and glutamic acid (acidic/savory component) aqueous solution. The change in frequency during 4 minutes after adding each of the solutions is shown in FIG. 6.

As shown in FIG. 5, when the astringency evaluating apparatus provided with a gelatin sensor was used, the change in frequency was greater with increasing catechin concentration, thus confirming adequately precise measurement of the change in frequency corresponding to the amount of formation of complex between catechin and gelatin. Also, as shown in FIG. 5 and FIG. 6, when solutions containing astringent components such as catechin, quercetin and epicatechin were used a notable change in frequency was observed, but when solutions containing no astringent components were used, virtually no change in frequency was observed.

(Beer Astringency Evaluation 1)

An astringency evaluating apparatus equipped with a gelatin sensor was used for measurement of the change in frequency upon addition of 0.5 ml each of two different beers A and B to 100 ml of distilled water. The results are shown in FIG. 7.

Figure 7:
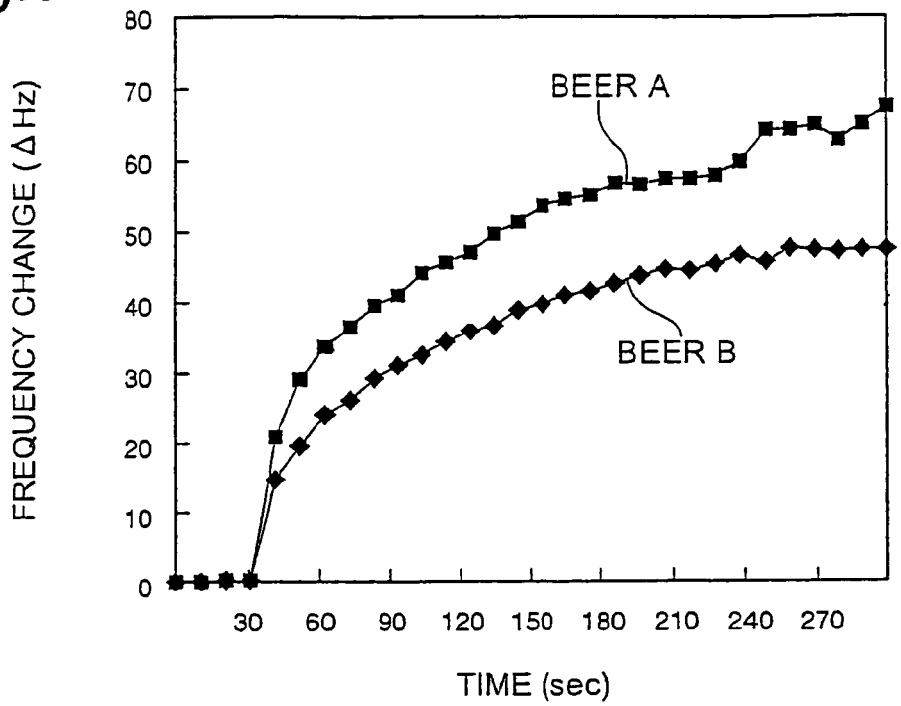
FIG. 7 is a graph showing the correlation between time and frequency change after addition of beers A and B, as obtained in Example 1.

An organoleptic evaluation test was carried out for beers A and B, giving results indicating strength of astringency in the order A, B, and confirming an adequately satisfactory correlation between the change in frequency and strength of astringency shown in FIG. 7.

(Beer Astringency Evaluation 2)

Figure 8:
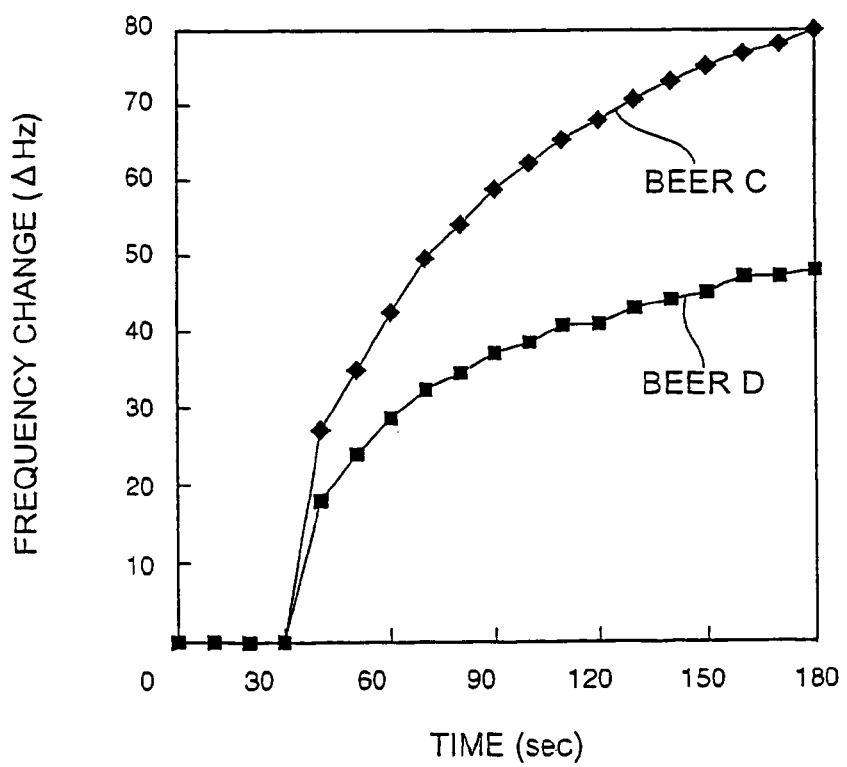
FIG. 8 is a graph showing the correlation between time and frequency change after addition of beers C and D, as obtained in Example 1.

An astringency evaluating apparatus equipped with a gelatin sensor was used for measurement of the change in frequency in the same manner as the frequency change measurement 1 described above, for beer C (polyphenol content: 173 mg/l, anthocyanidin content: 65 mg/l) and beer D obtained by PVPP treatment of beer C to reduce the content of polyphenols such as anthocyanidin (polyphenone 100 content: 76 mg/l, anthocyanidin content: 14 mg/l). The results are shown in FIG. 8. The PVPP treatment was adsorption removal of the polyphenols such as the tannic astringent components using polyvinylpolypyrrolidone.

An organoleptic evaluation test was carried out for beers C and D, giving results indicating strength of astringency in the order C, D, and confirming an adequately satisfactory correlation between the change in frequency and strength of astringency shown in FIG. 8.

Example 2

Fabrication of Astringency Evaluating Apparatus with Lipid Membrane Sensor

The electrode of a sensor equipped with a quartz oscillator (Fragrance Sensor SF-105, product of Sogo Pharmaceutical Co., Ltd.) was coated with a lipid membrane composed of dioctadecylammonium polystyrenesulfonic acid to obtain a lipid membrane sensor. This lipid membrane sensor was used to fabricate an astringency evaluating apparatus having the construction shown in FIG. 4.

(Correlation Between Amount of Complex Adsorption on to Lipid Membrane and Change in Frequency)

The obtained astringency evaluating apparatus was used for measurement of the change in frequency corresponding to adsorption on to the lipid membrane by complex between proline-rich peptide and tannic acid.

Figure 9:
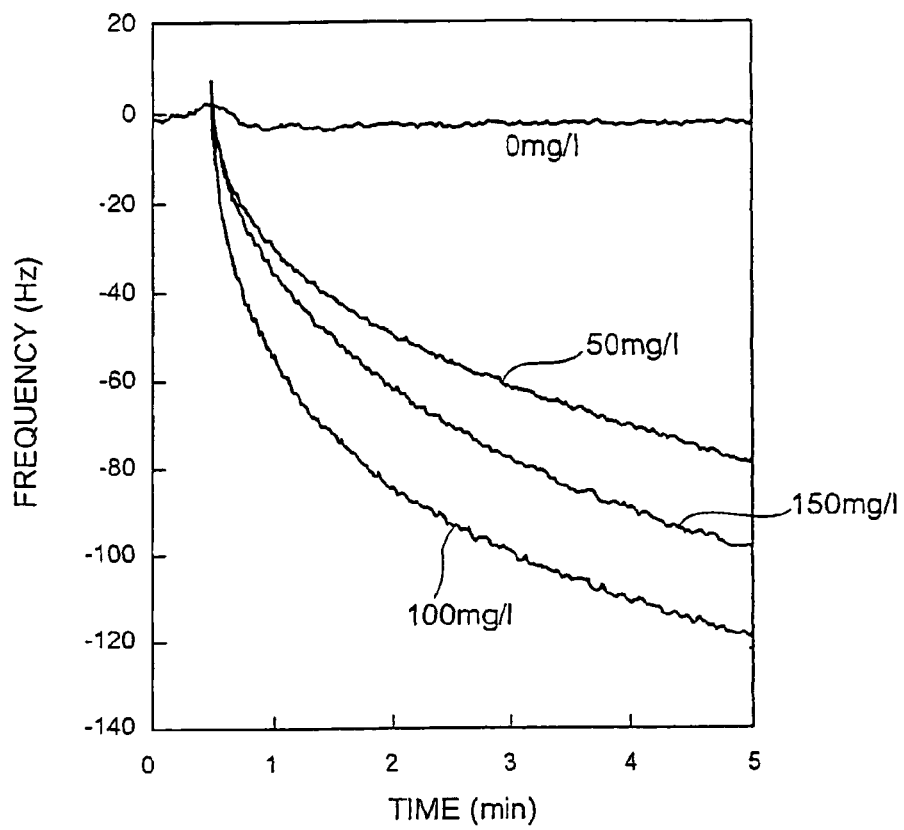
FIG. 9 is a graph showing the correlation between time and frequency change after addition of tannic acid, as obtained in Example 2.

First, the sensor element measuring section of the lipid membrane sensor was immersed in a 25 mM acetate buffer solution (pH 4.3) dissolving 50, 100 or 150 mg/l of mouse proline-rich peptide (Sawady Technologies), and stabilization of frequency was confirmed. Next, 0.1 ml of tannic acid was added to each mouse proline-rich peptide/acetate buffer solution, and the change in frequency was measured up to 5 minutes after addition. For the measurement, the tannic acid concentration of the buffer solution immediately after tannic acid addition was 8 mg/l. FIG. 9 shows the correlation between the time after addition of the tannic acid and the change in frequency, as obtained by the measurement.

Figure 10:
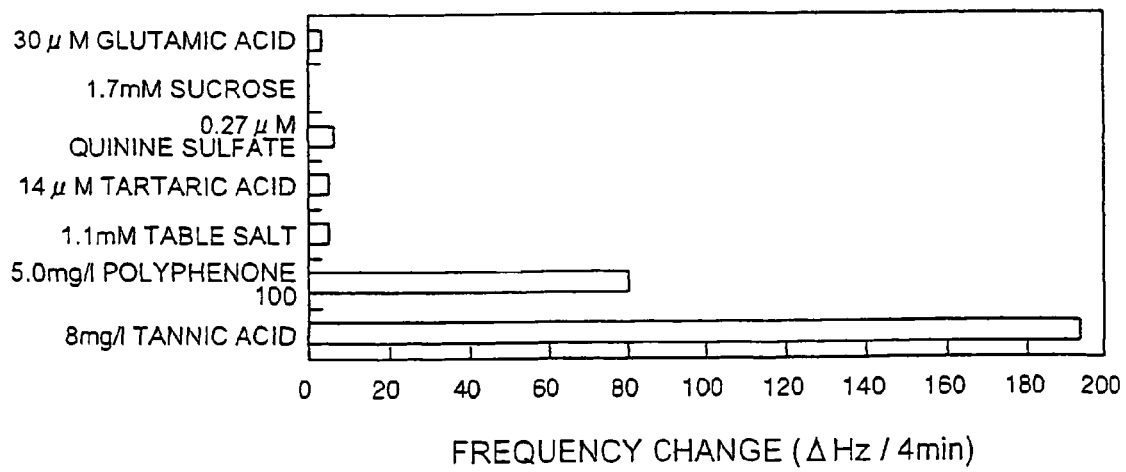
FIG. 10 is a graph showing the change in frequency during 4 minutes after adding different gustation components, using gelatin, as obtained in Example 2.
Figure 11:
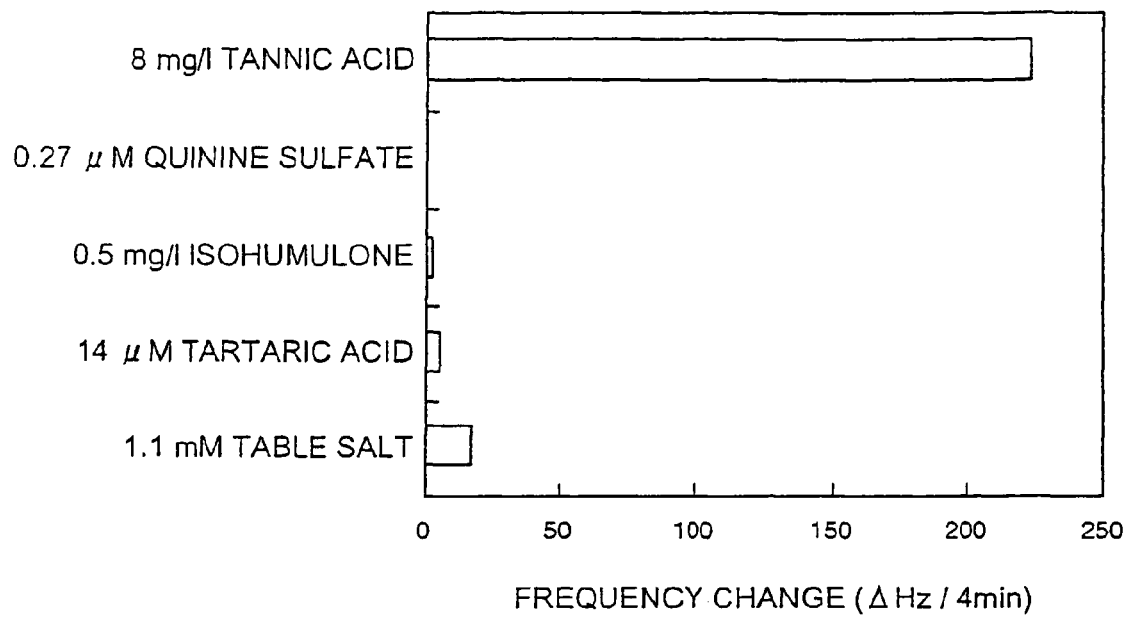
FIG. 11 is a graph showing the change in frequency during 4 minutes after adding different gustation components, using bovine serum albumin, as obtained in Example 2.

The change in frequency was also measured in the same manner as above except that gelatin (Aldrich Chemical Company, Inc.) or bovine serum albumin (Wako Junyaku Kogyo) was used instead of the mouse proline-rich peptide, and tannic acid (concentration after addition to buffer solution [hereunder referred to simply as "concentration in buffer solution"]: 8 mg/l, and polyphenone 100 (concentration in buffer solution: 50 mg/l) were added. As comparative tests, the same measurement was conducted using sucrose (sweet component, concentration in buffer solution: 1.7 mM), quinine sulfate (bitter component, concentration in buffer solution: 0.27 µM), tartaric acid (acidic component, concentration in buffer solution: 14 µM), NaCl (salty component, concentration in buffer solution: 1.1 mM) and glutamic acid (acidic/savory component, concentration in buffer solution: 30 µM). The change in frequency during 4 minutes after adding different components using gelatin is shown in FIG. 10. Also, the change in frequency during 4 minutes after adding different components using bovine serum albumin is shown in FIG. 11.

As shown in FIG. 9, when the astringency evaluating apparatus provided with a lipid membrane sensor was used, the change in frequency was greater with increasing tannic acid concentration, thus confirming adequately precise measurement of the change in frequency corresponding to the amount of adsorption on to the lipid membrane by the complex between tannic acid and mouse proline-rich peptide. Also, as shown in FIGS. 9-11, when solutions containing astringent components such as tannic acid and polyphenone 100 were used a notable change in frequency was observed, but when solutions containing no astringent components were used, virtually no change in frequency was observed.

(Correlation Between Astringent Component concentration and Change in Frequency)

Figure 12:
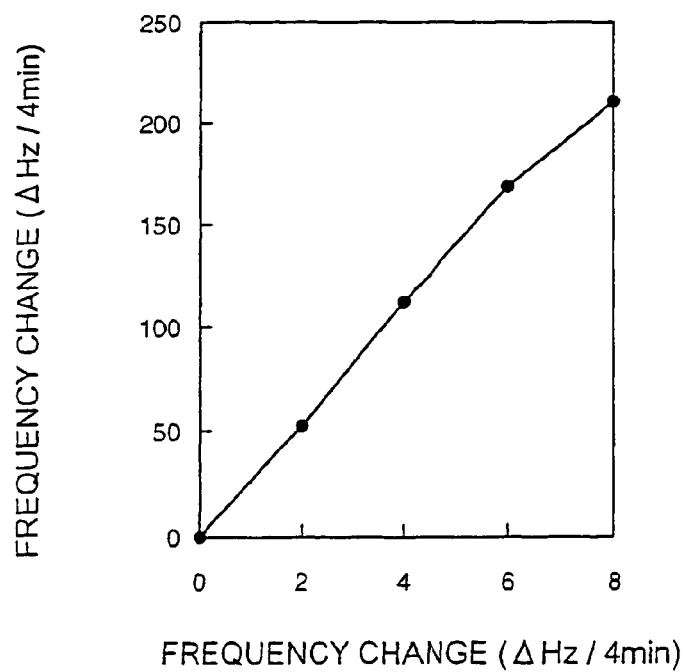
FIG. 12 is a graph showing the correlation between tannic acid concentration and frequency change, as obtained in Example 2.

In the above-mentioned frequency change measurement 1 using the astringency evaluating apparatus provided with a lipid membrane sensor, the change in frequency was measured with different tannic acid concentrations in 10 mg/l gelatin (Aldrich Chemical Company, Inc.)/25 mM acetate buffer solution, to determine the correlation between tannic acid concentration and change in frequency. The results are shown in FIG. 12. As seen in FIG. 12, an adequately satisfactory correlation was found between tannic acid concentration and change in frequency.

(Correlation Between Buffer Solution pH and Change in Frequency)

Figure 13:
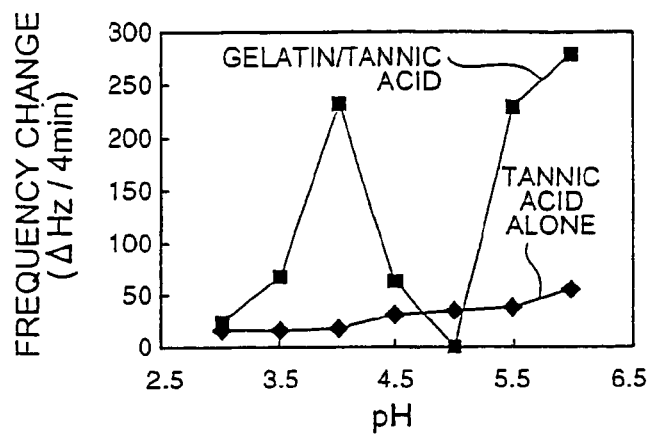
FIG. 13 is a graph showing the correlation between acetate buffer solution pH and frequency change, using gelatin, as obtained in Example 2.
Figure 14:
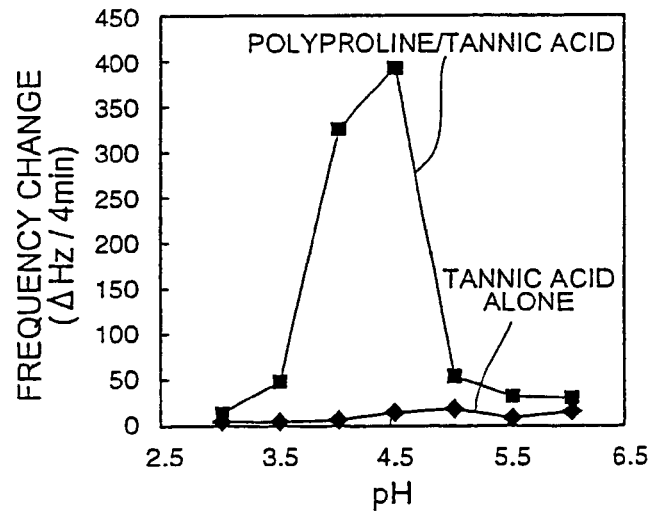
FIG. 14 is a graph showing the correlation between acetate buffer solution pH and frequency change, using poly-L-proline, as obtained in Example 2.
Figure 15:
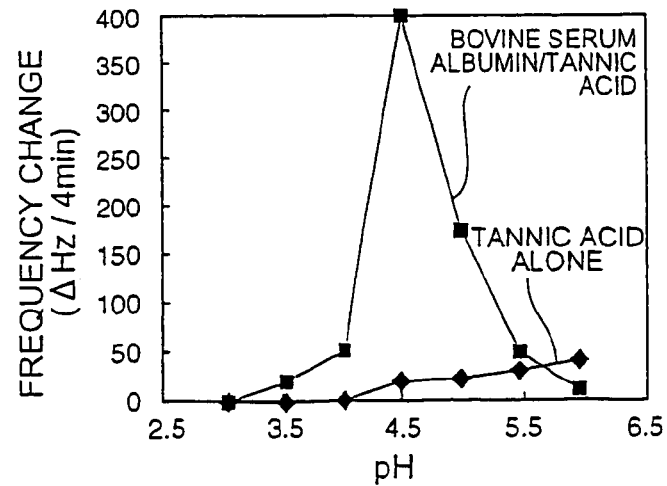
FIG. 15 is a graph showing the correlation between acetate buffer solution pH and frequency change, using bovine serum albumin, as obtained in Example 2.

The change in frequency was measured in the same manner as above except that gelatin (Aldrich Chemical Company, Inc.), poly-L-proline (weight-average molecular weight: 5000, product of SIGMA) or bovine serum albumin (product of Wako Junyaku Kogyo) was used and the pH of the acetate buffer solution was changed, in order to determine the correlation between acetate buffer solution pH and change in frequency. The results obtained using gelatin are shown in FIG. 13, the results obtained using poly-L-proline are shown in FIG. 14, and the results obtained using bovine serum albumin are shown in FIG. 15. FIGS. 13-15 also show the results for adsorption of tannic acid alone in the absence of the peptide.

As shown in FIGS. 13-15, a very large change in frequency was observed at pH 4.0 and pH 5.5-6.5 when gelatin was used, at pH 4.0-4.5 when poly-L-proline was used and at pH 4.3-5.0 when bovine serum albumin was used.

(Beer Astringency Evaluation)

An astringency evaluating apparatus equipped with a lipid membrane sensor was used for measurement of the change in frequency upon addition of 5 ml each of two different beers E and F to 95 ml of 10 mg/l gelatin/25 mM acetate buffer solution (pH 4.5). The results are shown in FIG. 16.

Figure 16:
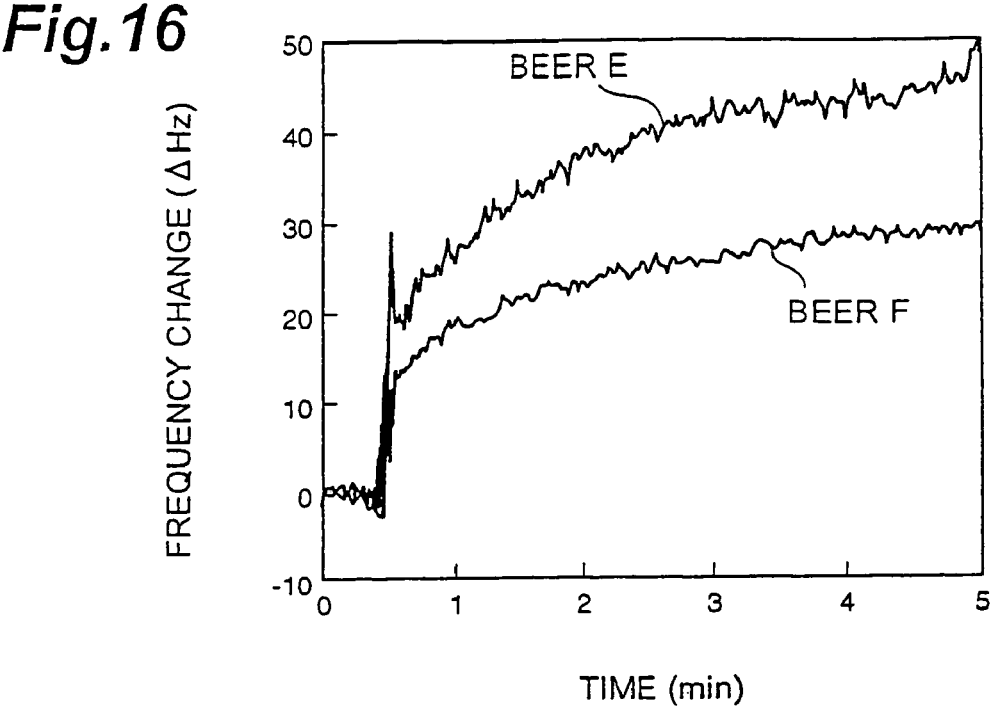
FIG. 16 is a graph showing the correlation between time and frequency change after addition of beers E and F to gelatin/acetate buffer solution, as obtained in Example 2.

An organoleptic evaluation test was carried out for beers E and F, giving results indicating strength of astringency in the order E, F, and confirming an adequately satisfactory correlation between the change in frequency and strength of astringency shown in FIG. 16.

Figure 17:
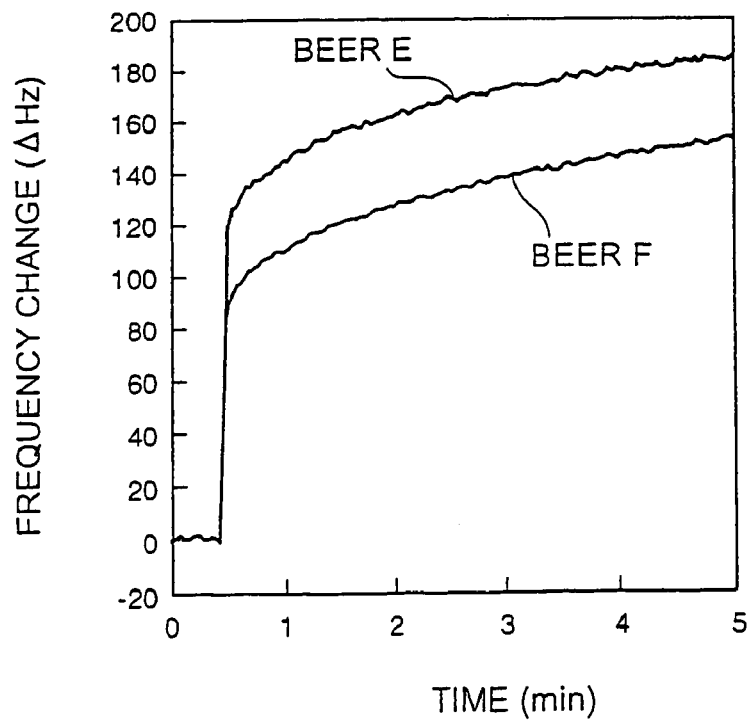
FIG. 17 is a graph showing the correlation between time and frequency change after addition of beers E and F to a gelatin aqueous solution, as obtained in Example 2.

The change in frequency was also measured with addition of beers E and F to a gelatin aqueous solution in the same manner as above except for using 95 ml of a 10 mg/l gelatin aqueous solution instead of the gelatin/acetate buffer solution. The results are shown in FIG. 17. As seen in FIG. 17, an adequately satisfactory correlation between strength of astringency and change in frequency was also exhibited in the organoleptic evaluation test when this gelatin aqueous solution was used.

(Wine Astringency Evaluation)

An astringency evaluating apparatus equipped with a lipid membrane sensor was used for measurement of the change in frequency upon addition of 0.1 ml each of two different wines G and H to 100 ml of a 10 mg/l bovine serum albumin aqueous solution. The results are shown in FIG. 18.

Figure 18:
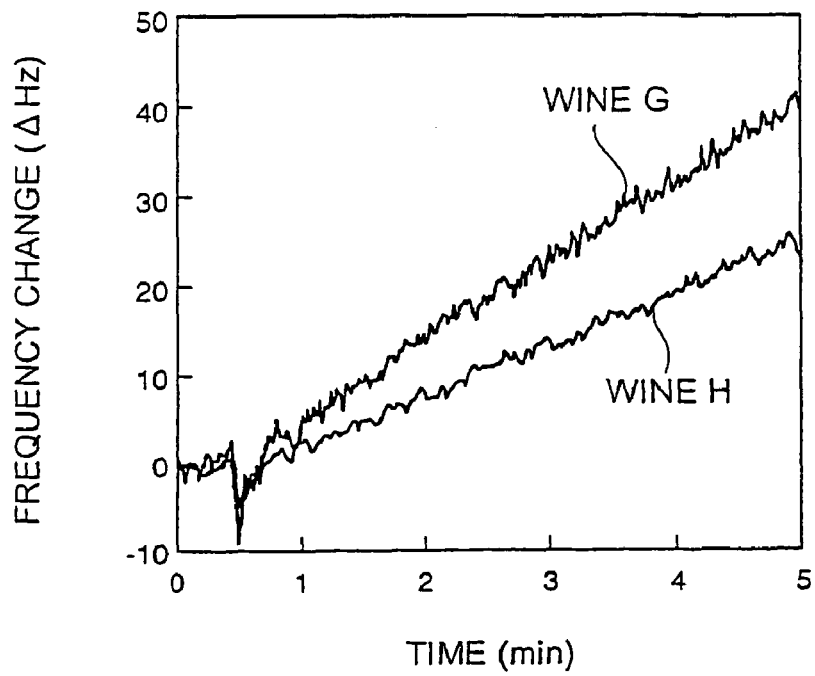
FIG. 18 is a graph showing the correlation between time and frequency change after addition of wines G in and H to a bovine serum albumin aqueous solution, as obtained in Example 2.
Figure 19:
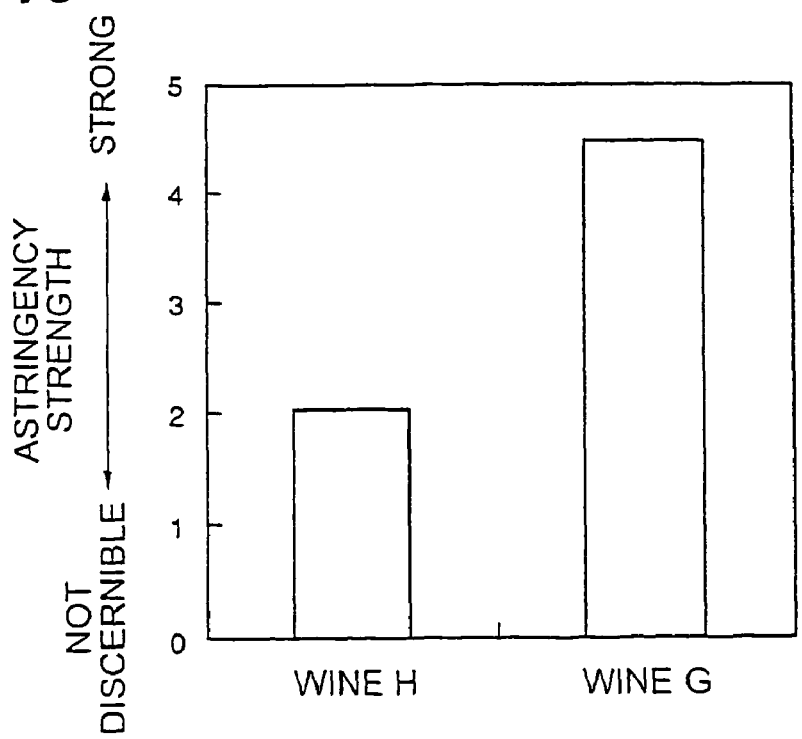
FIG. 19 is a graph showing the results of an organoleptic evaluation test of the astringency strength of wines G and H, as obtained in Example 2.

An organoleptic evaluation test was carried out for wines G and H, giving results indicating strength of astringency in the order G, H as shown in FIG. 19, and confirming an adequately satisfactory correlation between the change in frequency and strength of astringency shown in FIG. 18.

(Green Tea Astringency Evaluation)

An astringency evaluating apparatus equipped with a lipid membrane sensor was used for measurement of the change in frequency upon addition of 5 ml each of two different green teas I and J to 95 ml of 10 mg/l bovine serum albumin/25 mM acetate buffer solution (pH 4.5). The results are shown in FIG. 20.

Figure 20:
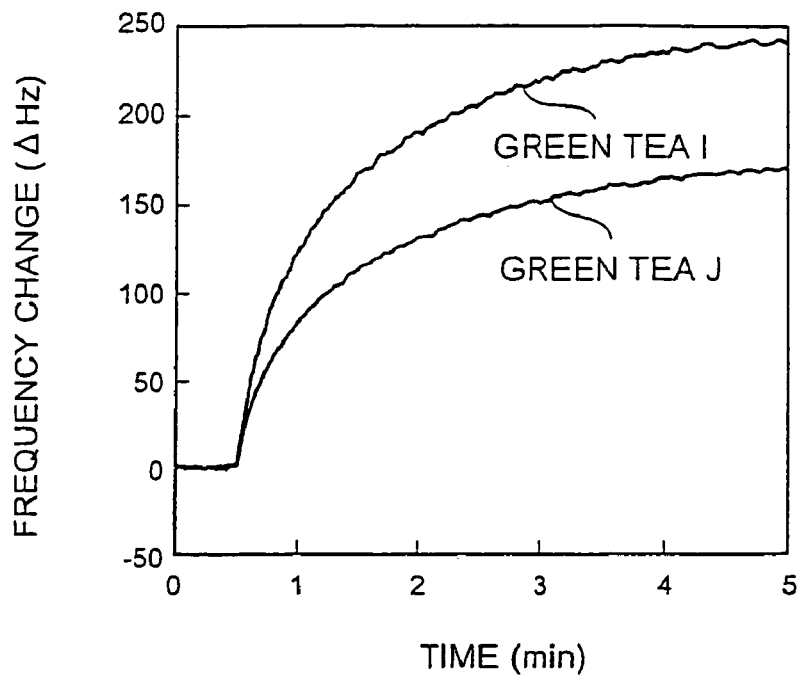
FIG. 20 is a graph showing the correlation between time and frequency change after addition of green teas I and J to bovine serum albumin/acetate buffer solution, as obtained in Example 2.
Figure 21:
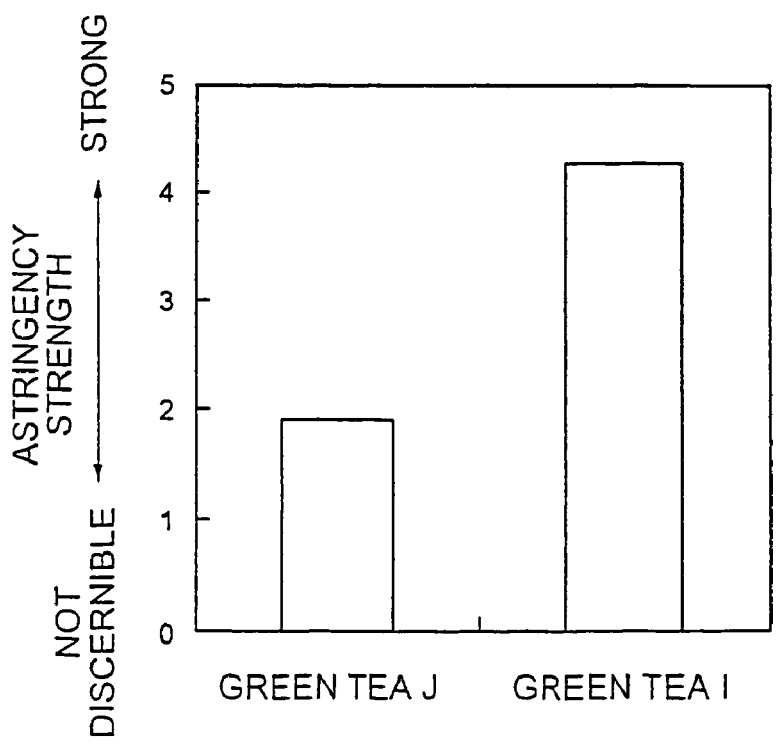
FIG. 21 is a graph showing the results of an organoleptic evaluation test of the astringency strength of green teas I and J, as obtained in Example 2.

An organoleptic evaluation test was carried out for green teas I and J, giving results indicating strength of astringency in the order I, J as shown in FIG. 21, and confirming an adequately satisfactory correlation between the change in frequency and strength of astringency shown in FIG. 20.

As explained above, according to the invention, a prescribed measured value corresponding to the amount of formation of the complex formed upon reaction of the astringent component of the food with the peptide, or to the amount of adsorption of the complex on to the lipid membrane, is obtained in a simple and easy manner, and with a high degree of reproducibility. In addition, with the data processing means it is possible to make an online determination of the strength of astringency from the obtained measured value based on a previously obtained correlation between strength of astringency and the prescribed measured value corresponding to the amount of formation or amount of adsorption of the complex. It is thereby possible to accomplish adequately precise and simple quantitative evaluation of astringency with the food astringency evaluating method and astringency evaluating apparatus of the invention.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A method for evaluating the astringency of a substance comprising:

contacting the substance to be evaluated for astringency with gelatin immobilized on a lipid membrane sensor with a quartz oscillator at a pH of 4.0 or 5.5 to 6.5 to form a complex, detecting complex formation between the substance and gelatin immobilized on a sensor, wherein the amount of complex formed measured by the sensor is conveyed to a data processing means which determines the astringency of the substance based on a previously obtained correlation between the strength of astringency and the amount of complex formation measured by the sensor.

2. The method of claim 1, wherein the substance contains at least one astringent component selected from the group consisting of tannic acid, citric acid, malic acid, catechin, epicatechin, epigallocatechin gallate, quercetin, anthocyanidin and polyphenone 100.

3. The method of claim 1, wherein the substance is a food.

4. The method of claim 1, wherein the substance is an alcoholic beverage.

5. The method of claim 1, wherein the substance is a food selected from the group consisting of beer, wine, or green tea.

6. The method of claim 1, wherein gelatin forms a complex with tannic acid, citric acid or malic acid.

7. The method of claim 1, wherein gelatin forms a complex with catechin, epicatechin, epigallocatechin gallate, quercetin, anthocyanidin or polyphenone 100 that is not a saliva protein.

8. The method of claim 1, wherein the amount of peptide is 100-15,000 parts by weight with respect to 100 parts by weight of the substance, the contacting temperature ranges from 20° C.-25° C., and the contacting time ranges from 0.5 to 10 minutes.

9. The method of claim 1, wherein said contacting occurs by immersing the sensor in a solution containing said substance.

10. The method of claim 1, wherein the substance is prepared in a water or buffer solution.

11. A method for evaluating the astringency of a substance comprising:

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 1

Gln Gly Pro Pro Pro Gln Gly Gly Pro Gln Gln Arg Pro Pro Gln Pro
1               5                   10                  15

Gly Asn Gln
``` contacting the substance to be evaluated for astringency with poly-L-proline immobilized on a lipid membrane sensor with a quartz oscillator at a pH of 4.0 to 4.5 to form a complex, detecting complex formation between the substance and poly-L-proline immobilized on a sensor, wherein the amount of complex formed measured by the sensor is conveyed to a data processing means which determines the astringency of the substance based on a previously obtained correlation between the strength of astringency and the amount of complex formation measured by the sensor.

12. The method of claim 11, wherein the substance contains at least one astringent component selected from the group consisting of tannic acid, citric acid, malic acid, catechin, epicatechin, epigallocatechin gallate, quercetin, anthocyanidin and polyphenone 100.

13. The method of claim 11, wherein the substance is a food.

14. The method of claim 11, wherein the substance is an alcoholic beverage.

15. The method of claim 11, wherein the substance is a food selected from the group consisting of beer, wine, or green tea.

16. The method of claim 11, wherein said contacting occurs by immersing the sensor in a solution containing said substance.

17. A method for evaluating the astringency of a substance comprising:

contacting the substance to be evaluated for astringency with bovine serum albumin immobilized on a lipid membrane sensor with a quartz oscillator at a pH of 4.3 to 5.0 to form a complex, detecting complex formation between the substance and bovine serum albumin immobilized on a sensor, wherein the amount of complex formed measured by the sensor is conveyed to a data processing means which determines the astringency of the substance based on a previously obtained correlation between the strength of astringency and the amount of complex formation measured by the sensor.

18. The method of claim 17, wherein the substance contains at least one astringent component selected from the group consisting of tannic acid, citric acid, malic acid, catechin, epicatechin, epigallocatechin gallate, quercetin, anthocyanidin and polyphenone 100.

19. The method of claim 17, wherein the substance is a food.

20. The method of claim 17, wherein the substance is an alcoholic beverage.

21. The method of claim 17, wherein the substance is a food selected from the group consisting of beer, wine, or green tea.

22. The method of claim 17, wherein said contacting occurs by immersing the sensor in a solution containing said substance.

* * * * *